United States Patent [19]

Hirao et al.

[11] Patent Number: 4,740,498

[45] Date of Patent: Apr. 26, 1988

[54] FIBRONECTIN PREPARATIONS

[75] Inventors: Yutaka Hirao; Takao Ohmura; Kazuo Takechi, all of Osaka; Tsunetaka Nakajima, Nara; Masayuki Nishida, Kyoto, all of Japan

[73] Assignee: Green Cross Corporation, Osaka, Japan

[21] Appl. No.: 790,668

[22] Filed: Oct. 23, 1985

[30] Foreign Application Priority Data

Oct. 24, 1984 [JP]  Japan ................................. 59-223731

[51] Int. Cl.[4] ..................... A61K 37/04; A61K 35/14; A61K 37/02
[52] U.S. Cl. ........................................ 514/8; 424/101; 514/2; 514/21; 530/380; 530/392; 530/394; 530/386
[58] Field of Search .................... 260/112 B; 424/101; 514/2, 8, 21; 530/380, 392, 394, 386; 604/595

[56] References Cited

U.S. PATENT DOCUMENTS

| | | | |
|---|---|---|---|
| 3,607,858 | 9/1971 | Querry et al. ................... | 260/112 B |
| 4,314,997 | 2/1982 | Shanbrom ......................... | 424/101 |
| 4,315,906 | 2/1982 | Geider ............................. | 260/112 B X |
| 4,315,919 | 2/1982 | Shanbrom ......................... | 514/1 |
| 4,412,990 | 11/1983 | Lundblad et al. ................. | 424/101 X |
| 4,424,206 | 1/1984 | Ohmura et al. .................. | 260/112 B X |
| 4,440,679 | 4/1984 | Fernandes et al. ................ | 260/112 B X |
| 4,478,829 | 10/1984 | Landaburu et al. ............... | 424/101 X |
| 4,481,189 | 11/1984 | Prince .............................. | 424/101 |
| 4,540,573 | 9/1985 | Neurath et al. .................. | 260/112 B X |
| 4,565,651 | 1/1986 | Ohmura et al. .................. | 260/112 B |
| 4,585,654 | 4/1986 | Landaburu et al. .............. | 424/101 |

FOREIGN PATENT DOCUMENTS

EPA-0035204  9/1981  European Pat. Off. .
EPA-0058993  9/1982  European Pat. Off. .
EPA-0124018  11/1984  European Pat. Off. .
EPA-0106608  4/1986  European Pat. Off. .

OTHER PUBLICATIONS

Nihon Ishikai Zasshi, vol. 91, 560–568 (1984)—English Translation.

Primary Examiner—Howard E. Schain
Attorney, Agent, or Firm—Sughrue, Mion, Zinn, Macpeak, and Seas

[57] ABSTRACT

A fibronectin preparation in the form of an aqueous solution at least upon use is disclosed. The preparation contains at least one member selected from the group consisting of disaccharides, albumin and nonionic surface active agents as a stabilizer. The preparation has improved water-solubility when in use and high stability in an aqueous solution.

6 Claims, No Drawings

FIBRONECTIN PREPARATIONS

FIELD OF THE INVENTION

This invention relates to improved preparations containing fibronectin as an active ingredient. More particularly, it relates to fibronectin preparations having incorporated therein a specific stabilizer and having the form of an aqueous solution at least upon use.

BACKGROUND OF THE INVENTION

Fibronectin (hereinafter simply referred to as FN) is a glycoprotein having a molecular weight of from 430,000 to 450,000. Fibronectin is present in the cell surface, connective-tissue membranes, blood, etc. of animals.

It is known that FN has the same relative mobility as $\alpha_2$-globulin, an isoelectric point of 5.0, a molecular extinction coefficient $A_{1\ cm}{}^{1\%}$ 280 nm of 12.9 to 13.0, $S_{20,w}$ of 11 to 14S, and a sugar content of 5%.

In blood coagulation, bonding between $\gamma$-chains of fibrin is accelerated by transglutaminase activity of blood coagulating factor XIII to form bridges of fibrin. At the same time, bridges of fibrin between $\alpha$-chains are formed through FN by the catalyzing activity of the same blood coagulating factor XIII, whereby complete blood coagulation is ensured. Further, FN exhibits an activity to adhere or bind cells or sustentacular tissues among each other and is, therefore, effective to promote repairment of injuries. Other pharmacological activities of FN that have hitherto been reported include a therapeutic effect on septic shock, a therapeutic effect on infectious diseases that is attributed to heightened opsonification of phagocytes, as well as anticancer and antileukemic activity attributable to its ability to increase adhesion among cells and to necrose cancer cells. Hence, great expectations are put on FN for its clinical effects as a drug.

Moreover, in the field of ophthalmology, it has been reported in *Nihon Ishikai Zasshi*, Vol. 91, 560–568 (1984) that FN is effective in the therapy of various disturbances of the corneal epithelium including herpetic ulcers of the cornea.

However, FN is labile in an aqueous solution. In other words, FN in the form of an aqueous solution has low stability in terms of its biological activities and cannot be preserved as such for a long period of time. Further, when FN-containing preparations formulated into dry products are dissolved in water upon use, turbidity appears in the aqueous solution due to poor water-solubility of FN. Thus, under these circumstances, FN preparations in the form of an aqueous solution for, inter alia, eye drops having sufficient stability for clinical application have not yet been obtained.

SUMMARY OF THE INVENTION

An object of this invention is to provide a stable preparation containing FN as an active ingredient which is in the form of an aqueous solution at least when in use.

Another object of this invention is to provide a stable preparation containing FN as an active ingredient which exhibits excellent water-solubility even when formulated into a dry preparation.

Extensive investigations have been conducted in order to realize the above objects and, as a result, it has now been found that stable FN aqueous solution preparations can be obtained by incorporating a specific stabilizer and that dry products of such FN preparations exhibit excellent water-solubility. The present invention has been completed based on this finding.

That is, the present invention relates to fibronectin preparations in the form of an aqueous solutions at least upon use, which contain at least one member selected from disaccharides, albumin and nonionic surface active agents.

DETAILED DESCRIPTION OF THE INVENTION

FN which can be used in the present invention can generally be separated from fractions of plasma-protein, fibroblast and its culture, etc.

In the present invention, FN to be used should be purified to such an extent that it can be provided as a drug and preferably has a protein content of at least 80%, more preferably at least 90%, by weight. For example, FN obtainable by a process for preparing cold inactive globulin established by the present inventors as disclosed in Japanese Patent Application (OPI) No. 121220/83, FN obtainable by heat-treatment of starting material at 60° C. for 10 hours for inactivation of hepatitis virus as disclosed in U.S. Pat. No. 4,424,206, and the like can be employed.

The disaccharides which can be used as a stabilizer in the present invention include sucrose, maltose, lactose, and the like, with sucrose being preferred.

Albumin which can be used as a stabilizer in the present invention is preferably originated from humans in view of antigenicity, and is not particularly restricted so long as purified for medical use. The preferred purity of albumin is 80% or more as analyzed by electrophoresis. Methods for obtaining albumin originating from humans include ethanol fractionation as described in Japanese Patent Publication Nos. 2869/72 and 5297/60, heat treatment in the presence of an organic acid as described in Japanese Patent Publication No. 40132/76 and U.S. Pat. No. 3,378,533 and the like. In particular, albumin having been subjected to heat treatment, preferably at 60° C. for about 10 hours, to inactivate heptatitis virus, etc. is preferred.

The nonionic surface active agents which can be used as a stabilizer in the present invention include polyalkylene glycols, polyol, fatty acid esters, polyol fatty acid ester-polyoxyalkylene condensates, polyoxyalkylene copolymers, and the like. Those having an average molecular weight of from 2,000 to 20,000 are preferred. More preferably, those having an average molecular weight of from 5,000 to 10,000 are used. Specific examples of the preferred nonionic surface active agents include a polyoxyethylene-polyoxypropylene copolymer having an average molecular weight of 8,400 ("Pluronic F68", a trade name manufactured by Wyandotte Chemicals Corp.).

These stabilizers can be used either alone or in combinations thereof, but, it is preferable to use Pluronic F68 alone or a combination of sucrose and albumin.

Since the above-described stabilizers improve stability of an FN aqueous solution and water-solubility of FN, the FN preparations according to the present invention covers not only aqueous solution preparations but also preparations that are formed into aqueous solutions when in use.

The FN preparations according to the present invention are suitably in the form of eye drops. Solvents for eye drops are not particularly limited as far as they provide isotonic solutions of pH 6 to 7. Specific examples of the solvents are a phosphate buffer, a borate buffer, physiological saline and the like. These solvents are desirably sterilized.

Eye drops usually comprise 250 to 1,000 μg/ml, preferably 250 to 500 μg/ml, of FN and a stabilizer, e.g., a disaccharide (10 to 50 mg/ml, preferably 25 to 50 mg/ml), albumin (50 to 1,000 μg/ml, preferably 100 to 500 μg/ml) or a nonionic surface active agent (20 to 500 μg/ml, preferably 20 to 100 μg/ml).

The eye drops of the present invention include not only general liquid preparations comprising FN and the stabilizer dissolved in a solvent but dry preparations comprising dried FN and stabilizer that are dissolved upon use.

The FN preparation of the present invention can be prepared by mixing fibronectin with at least one member selected from the group consisting of disaccharides, albumin and nonionic surface active agents and optionally a solvent. The mixing can be carried out in a conventional manner. In the case of preparing dry preparations which are dissolved in a solvent upon use, the dry products may be prepared by compounding dried FN with a dried stabilizer or lyophilizing an aqueous solution of FN and a stabilizer. The compounding and lyophilizing can be performed in a conventional manner.

The eye drops of the present invention can further contain pharmaceutically acceptable additives commonly employed for eye drops, such as a antiseptics, e.g., methyl p-hydroxybenzoate, propyl p-hydroxybenzoate, sodium dehydroacetate, methylosal, etc.

The eye drops of the present invention can be preserved even in the form of an aqueous solution at room temperature, but is preferably preserved at lower temperatures, e.g., around 4° C.

Since the stabilizers which can be used in the present invention improve stability of FN in an aqueous solution, the FN preparations according to the present invention retain high stability even in the form of an aqueous solution. In addition, these stabilizers improve water-solubility of dry FN preparations when in use.

When applied to the ophthalmologic area, the FN preparations of the present invention are effective in the treatment of disturbances in the corneal epithelium including the following diseases:
1. Trophic ulcer (herpetic and paralytic)
2. Continuous epithelium defect (herpetic)
3. Palindromic erosion (herpetic and traumatic)
4. Reduction of tears
5. Epithelial disturbances after the operation of the vitreous body in diabetics
6. Steven-Johnson's syndrom The eye drops of the present invention are generally instilled directly in the conjunctival sac.

The dosage of the FN preparations can appropriately be selected according to the kind of diseases, symptoms, the age of patients, etc. as in the conventional FN preparation. When the FN preparation of this invention is in the form of eye drps, it is preferred that the preparation be administered in an amount of 10 to 1,000 μg/day, preferably 100 to 500 μg/day, in terms of FN. The daily dosage can be administered at a time or dividedly (preferably 2 to 10 times/day).

The present invention will now be illustrated in greater detail with reference to the following examples and test examples, but it should be understood that these examples are in now way intended to limit the present invention.

EXAMPLE 1

Eye drops comprising the following ingredients were prepared in a usual manner.

| | |
|---|---|
| FN | 500 mg |
| Sucrose | 50 g |
| Albumin | 250 mg |
| Sodium chloride | 8.5 g |
| Sodium primary phosphate dihydrate | 1.14 g |
| Sodium secondary phosphate dodecahydrate | 1.08 g |
| Distilled water to make | 1000 ml (pH 6.5) |

The resulting FN eye drops were poured into vials in 2 ml portions and lyophilized. The lyophilized preparation was dissolved in distilled water to make 2 ml upon clinical use to obtain stable FN eye drops.

EXAMPLE 2

Eye drops comprising the following ingredients were prepared in a usual manner.

| | |
|---|---|
| FN | 500 mg |
| Pluronic F68 (polyoxyethylene-polyoxypropylene copolymer, average molecular weight: 8350) | 20 mg |
| Sodium chloride | 8.5 g |
| Sodium primary phosphate dihydrate | 1.14 g |
| Sodium secondary phosphate dodecahydrate | 1.08 g |
| Distilled water to make | 1000 ml (pH 6.5) |

TEST EXAMPLE 1

Water-Solubility

The water-solubility of the FN lyophilized preparation as obtained in Example 1 was evaluated as follows.

Each of the compositions shown in Table 1 below was dissolved in an isotonic phosphoric acid buffer, followed by lyophilization. The lyophilized product was dissolved in 2 ml of distilled water, and the solubility was observed. The results obtained are shown in Table 2.

TABLE 2

| Composition | | Distilled Water | Solubility |
|---|---|---|---|
| FN | 1,000 μg | 2 ml | Slight turbidity appeared; a large quantity of an insoluble matter was observed. |
| FN + Sucrose | 1,000 μg 100 mg | 2 ml | Dissolution required time (5 to 10 mins.); transparent; an insoluble matter was slightly observed. |
| FN + Albumin | 1,000 μg 500 μg | 2 ml | Slight turbidity appeared; an insoluble matter was observed. |
| FN + Sucrose + Albumin | 1,000 μg 100 mg 500 μg | 2 ml | Dissolution instantaneously completed; transparent; no insoluble matter was observed. |

TEST EXAMPLE 2

Stability in Solution

Each of (A) a solution of FN in distilled water, (B) a solution of the FN lyophilized preparation obtained in Example 1 in distilled water, (C) the FN liquid preparation obtained in Example 2 and (D) an FN liquid preparation prepared in the same manner as in Example 2 but additionally containing sucrose was preserved at 4° C. or room temperature for 4 weeks to examine stability. The results are shown in Table 2 below.

TABLE 2

| Sample | Composition | | Stability |
|---|---|---|---|
| A | FN | 500 μg/ml | A white filamentous precipitate was formed. |
| B | FN | 500 μg/ml | No change was observed. |
|   | Sucrose | 50 mg/ml |   |
|   | Albumin | 250 μg/ml |   |
| C | FN | 500 μg/ml | " |
|   | Pluronic F68 | 20 μg/ml |   |
| D | FN | 500 μg/ml | " |
|   | Sucrose | 50 mg/ml |   |
|   | Pluronic F68 | 20 μg/ml |   |

TEST EXAMPLE 3

Toxicity

Each of the FN eye drops prepared in Example 1 and Example 2 was intravenously, orally or subcutaneously administered to mice and rats to determine acute toxicity. As a result, no abnormality was observed at a dose of 2,000 mg/Kg either in rats or mice, indicating extremely low toxicity of these preparations.

TEST EXAMPLE 4

Toxicity of Administration in the Eyes

Toxicity of the FN eye drops prepared in Examples 1 and 2 in instillation in the eyes was determined according to the method of Draize using white domestic rabbits (*Dokusei Shiken Handbook* (Toxicity Test Handbook), pp 297-303, Fuji Technosystem (1980)). As a control. physiological saline was used. It was revealed that the toxicity of the FN eye drops of this invention was equal to that of physiological saline.

TEST EXAMPLE 5

Pharmacological Effect

The therapeutic effect of the FN preparations of the present invention was examined using a model of corneal disturbance in rabbits. The model was prepared by applying liquid nitrogen to the eyes of rabbits to cause refrigeration trauma on the corneal epithelium. The FN eye drops prepared in Example 2 were administered into the eyes thus suffering from corneal disturbance at a dose of 400 μg-FN/ml, and the wound surface area was measured with the passage of time. As a control, 400 μg/ml of albumin was used. The results obtained are shown in Table 3 below.

TABLE 3

| Active Ingredient | Dose (μg/ml) | Wound Surface Area (mm$^2$) | | | | |
|---|---|---|---|---|---|---|
|   |   | 0 Day | 1 Day | 2 Days | 3 Days | 4 Days |
| Albumin | 400 | 45 | 31 | 33 | 25 | 14 |
| FN | 400 | 45 | 18 | 3 | 0 | 0 |

It can be seen from Table 3 above that the FN-treated group shows higher rate of reduction of the wound in size than that of the control group, indicating more rapid repairment of the wound.

While the invention has been described in detail and with reference to specific embodiments thereof, it will be apparent to those skilled in the art that various changes and modifications can be made therein without departing from the spirit and scope thereof.

What is claimed is:

1. A fibronectin preparation in the form of an aqueous isotonic eyedrop solution having a pH of 6 to 7, which contains 250 to 1,000 μg/ml of substantially pure fibronectin as an active ingredient and 20 to 500 μg/ml of polyoxyethylene-polyoxypropylene copolymer nonionic surface active agent as a stabilizer, said preparation not containing a carbohydrate.

2. The fibronectin preparation as claimed in claim 1, wherin the nonionic surface active agent has an average molecular weight of from 2,000 to 20,000.

3. The fibronectin preparation as claimed in claim 1, wherein the amount of said nonionic surface active agent in an aqueous solution is from 20 to 100 μg/ml.

4. A process for preparing a stable isotonic eyedrop solution of fibronectin having a pH of 6 to 7 which comprises admixing in aqueous solution 250 to 1,000 μg/ml of substantially pure fibronectin as an active ingredient and 20 to 500 μg/ml of polyoxyethyelene-polyoxypropylene copolymer nonionic surface active agent as a stabilizer, said process not including use of a carbohydrate and regulating the pH of said solution to be within pH 6 to 7.

5. The process of claim 4, wherein the amount of said nonionic surface active agent in an aqueous solution is from 20 to 100 μg/ml.

6. The process of claim 4, wherein the nonionic surface active agent has an average molecular weight of from 2,000 to 20,000.

* * * * *